(12) United States Patent
Deckmann

(10) Patent No.: US 7,354,991 B2
(45) Date of Patent: Apr. 8, 2008

(54) PEPTIDES FOR THE DIAGNOSIS OF SCHIZOPHRENIA

(75) Inventor: Michael Deckmann, deceased, late of Guebwiller (FR); by Jonathan Leitersdorf, legal representative, Geneva (CH)

(73) Assignee: Yeda Research and Development Co. Ltd, Rehovot (IL)

( * ) Notice: Subject to any disclaimer, the term of this patent is extended or adjusted under 35 U.S.C. 154(b) by 316 days.

(21) Appl. No.: 10/472,582

(22) PCT Filed: Mar. 21, 2002

(86) PCT No.: PCT/IL02/00233

§ 371 (c)(1),
(2), (4) Date: Oct. 7, 2004

(87) PCT Pub. No.: WO02/074793

PCT Pub. Date: Sep. 26, 2002

(65) Prior Publication Data

US 2005/0089927 A1   Apr. 28, 2005

(30) Foreign Application Priority Data

Mar. 21, 2001 (IL) .................................... 142159

(51) Int. Cl.
*C07K 17/14* (2006.01)
*C07K 7/05* (2006.01)
*G01N 33/53* (2006.01)

(52) U.S. Cl. ................. 530/300; 435/7.1; 436/503; 424/185.1

(58) Field of Classification Search .................. None
See application file for complete search history.

(56) References Cited

U.S. PATENT DOCUMENTS 6,008,001 A   12/1999   Shinitzky

FOREIGN PATENT DOCUMENTS

| WO | WO 92/18644 | 10/1992 |
|----|-------------|---------|
| WO | WO 95/12685 | 5/1995  |
| WO | WO 95/23970 | 9/1995  |
| WO | WO 99/30163 | 6/1999  |
| WO | WO 99/51725 | 10/1999 |
| WO | WO 00/06723 | 2/2000  |

OTHER PUBLICATIONS

UniProt Q9SVH3, internet printout from Oct. 31, 2006.*
Vermuyten, K. et al. "Detection of neuron specific enolase concentrations in cerebrospinal fluid from patients with neurological disorders by means of a sensitive enzyme immunoassay", *Clinica Chimica Acta*, Elsevier Science Publishers B.V., vol. 187 pp. 69-78, 1990.
Deckmann, M. et al. "A conformational epitope which detects autoantibodies from schizophrenic patients", *Clinica Chimica Acta*, Elsevier Science B.V., vol. 322 pp. 91-98, 2002.
Shinitzky, M. et al. "Platelet Autoantibodies in Dementia and Schizophrenia", Ann. NY Acad. Sci., vol. 621 pp. 205-217, 1991.
Rotman, A. "Blood Platelets in Psychopharmacological Research", *Prog. Neuro-Psychopharmacol & Biol. Psychiat.*, Pergamon Press ltd., vol. 7 pp. 135-151, (1983).
Deckmann, M. et al. "Humoral and cellular response against autologous platelets in schizophrenia. Clinical and pathophysiological implications", *The Italian Journal of Psychiatry and Behavioral Sciences*, Idelson Scientific Publications, vol. 6(2) pp. 29-34, (1996).
Carpenter, W. et al. "Schizophrenia", *The New England Journal of Medicine*, vol. 330(10) pp. 681-690, (1994).

* cited by examiner

*Primary Examiner*—Robert C. Hayes
*Assistant Examiner*—Daniel E Kolker
(74) *Attorney, Agent, or Firm*—The Nath Law Group; Gary M. Nath; Susanne M. Hopkins

(57) ABSTRACT

Short peptides are provided, which bind to a body fluid sample obtained from a schizophrenic patient at a substantively higher level than to a body fluid sample obtained from a non-schizophrenic individual. The peptides are no more than 10 amino acids long and comprise a continuous sequence of at least 5 amino acids which consists of at least one positively charged amino acid at one of its ends. The provided peptides, which are the putative binding sites of autoantibodies found in high levels in schizophrenic individuals, are thus useful in diagnosis of schizophrenia.

11 Claims, 4 Drawing Sheets

SEQUENCE LISTING

```
<160> NUMBER OF SEQ ID NOS: 4

<210> SEQ ID NO 1
<211> LENGTH: 7
<212> TYPE: PRT
<213> ORGANISM: Homo Sapiense

<400> SEQUENCE: 1

Leu Val Val Gly Leu Cys Lys
1               5

<210> SEQ ID NO 2
<211> LENGTH: 7
<212> TYPE: PRT
<213> ORGANISM: Homo Sapiense

<400> SEQUENCE: 2

Lys Leu Val Val Gly Leu Cys
1               5

<210> SEQ ID NO 3
<211> LENGTH: 7
<212> TYPE: PRT
<213> ORGANISM: Homo Sapiense

<400> SEQUENCE: 3

Leu Val Val Gly Leu Met Lys
1               5

<210> SEQ ID NO 4
<211> LENGTH: 7
<212> TYPE: PRT
<213> ORGANISM: Homo Sapiense

<400> SEQUENCE: 4

Lys Leu Val Val Gly Leu Met
1               5
```

PEPTIDES FOR THE DIAGNOSIS OF SCHIZOPHRENIA

FIELD OF THE INVENTION

The present invention concerns an assay for the diagnosis of schizophrenia and provides novel peptides for use in the assay.

PRIOR ART

The following is a list of publications intended for better understanding of the Background of the Invention. The acknowledgement herein of the above prior art should not be construed as an indication that this art is in any way relevant to the patentability of the invention as defined in the appended claims.

Carpenter, W. T., and Buchanan, R. W.: Review, N. England., *J Med.*, 330:681-690, 1994.

Deckmann, M., Shinitzky, M., Leykin, I., Cheng, D., Guy, J., Avnon, M., Salganik, I., Amiri, Z., Schlossberg, A., Leibu, E., and Rafael, C.: *The Italian J. Psychiatr. Behav. Sci.*, 6:29-34, 1996.

DeLisi, L. E. and Crow, T. J.: *Psychiatr North Am.*, 9:115-132, 1987.

Rotman, A.: Blood platelets in psychopharmacological research. *Prog. Neuropsychopharmacol.*, 6:135-151, 1983.

Shinitzky, M., Deckmann, M., Kessler, A., Sirota, P., Rabbs, A., and Elizur, A.: *Ann. N.Y. Acad. Sci.*, 621: 205-217, 1991.

Shinitzky, M., and Deckmann, M., "Diagnosis of the susceptibility of contracting schizophrenia", U.S. Pat. No. 6,008,001, 1999.

Shinitzky, M., and Deckmann, M., "Assay for schizophrenia based on skin reaction" WO 99/30163, 1999.

Shinitzky, M., and Deckmann, M., "Assay for the diagnosis of schizophrenia based on a new peptide" WO 99/51725, 1999.

BACKGROUND OF THE INVENTION

Schizophrenia is a syndrome which encompasses a variety of mental symptoms like auditory hallucinations, paranoia, delusions, catatonia, bizarre behavior and emotional withdrawal. Schizophrenia affects about 1% of the total population and its economical as well as social burden on society are enormous. The onset of the disease occurs in early age and, thus, patients typically need life-long medical and psychiatric supervision. Schizophrenia is, therefore, rated as one of the most costly diseases in the industrial world (Carpenter, et al., 1994).

No common parameter associated with schizophrenia has been identified and, therefore, the internationally agreed diagnosis of this disease is still based today solely on psychiatric evaluation. Known risk factors associated with schizophrenia, are genetic predisposition, birth during winter and complications during pregnancy or birth. Viral and/or bacterial infections with a subsequent autoimmune reaction have been proposed as causative factors for the increasing outbreak of schizophrenia (DeLisi, et al, 1987).

Schizophrenia has been shown to involve an autoimmune process and lately autoantibodies and cytotoxic T-cells against platelets were demonstrated in schizophrenic patients (Shinitzky, 1991, Deckmann, 1996, Shinitzky, 1999, U.S. Pat. No. 6,008,001). The cytotoxic T-cell reaction in schizophrenic patients was evaluated by a skin test in which most schizophrenic patients reacted positively against their autologous platelets whereas only a very minor number of non-schizophrenic tested individuals reacted positively in this test (Shinitzky, 1999, WO 99/30163).

In addition elevated levels of autoantibodies against platelets were observed in schizophrenic patients but not in patients suffering from manic-depressive disorder, depression, personality disorders and schizoaffective disorder (Shinitzky, 1991 and Deckmann, 1996).

In the inventors' prior work several proteins which bind autoantibodies that are found in elevated levels in body fluids of schizophrenic patients were identified (Shinitzky et al, 1999, WO 99/51725). These proteins reacted with purified platelet derived autoantibodies (PAA) from schizophrenic patients but could not differentiate between plasma or blood samples of schizophrenic and non-schizophrenic individuals. Enzymatic digestion of one of these proteins, the enzyme Enolase, resulted in a fragment which bound to plasma samples of schizophrenic patients substantially higher than it bound to plasma samples of non-schizophrenic individuals. On the basis of this fragment several additional peptides were synthesized and such having a high binding activity to PAAs of schizophrenic individuals were isolated. The structure of the antigenic epitope of these peptides was found to be a three-dimensional epitope which, by using a computerized program was predicted to be a cyclic structure comprising a hydrophobic core and an extension having about two positive charges. Immunological studies demonstrated that only the oxidized cyclic form of the peptide was reactive with the anti-platelet autoantibodies. These synthesized peptides comprised at least 17 amino acids (a.a.).

SUMMARY OF THE INVENTION

In accordance with the present invention, it has been realized that the peptide sequences described in the prior art (WO 99/51725) are able to bind to a higher extent to autoantibodies which are found in elevated levels in body fluids of schizophrenic patients and to a lower extent or not at all in body fluids of non-schizophrenic individuals, but these peptides cannot be the natural binding site for such autoantibodies. This is due to the fact that the sequences are not exposed on the surface of the protein from which they were derived (the enzyme enolase). Except for the single amino acid arginine at position 402, the remaining amino acids are buried inside the protein (see FIG. 1). In addition, as known, an antibody binding site is usually comprised of about 5-8 a.a. while each of these peptides comprised 17 a.a. which are not all necessary for the binding site.

Therefore, in accordance with the present invention, based on the realization that the peptide which is the natural binding site for autoantibodies found in elevated levels in schizophrenic patients will have a more sensitive and specific binding to such autoantibodies and as such may be advantageous in diagnosis of schizophrenia, an attempt was made to identify an equivalent site on the surface of the enolase by using three-dimensional modeling. Using the three-dimensional structure to search the surface of the enolase resulted in the identification of a putative epitope (see FIG. 2) consisting of four positively charged amino acids defined as R414, R184, K194 and R402 which surround a cluster of neutral amino acids defined as L412, L 183, L409, L406, P400 and A401. Peptides having such a putative epitope are provided in accordance with the invention.

Thus, by its first aspect, the present invention provides a peptide which binds to a body fluid sample obtained from a schizophrenic patient at a substantively higher level than its binding to a body fluid sample obtained from a non-schizophrenic individual, said peptide being no more than 10 amino acids (a.a.) long and comprising a continuous sequence of at least 5 amino acids included in any one of the following sequences:

```
i.      LVVGLCK     (SEQ ID NO. 1)
ii.     KLVVGLC     (SEQ ID NO. 2)
iii.    LVVGLMK     (SEQ ID NO. 3)
iv.     KLVVGLM;    (SEQ ID NO. 4)
``` said continuous sequence consisting of at least one positively charged a.a. at one end of said sequence; and said peptide comprising at least one positively charged a.a at its end being the positively charged a.a of said continuous sequence or at least one additional positively charged a.a.; or analogues of said peptide being no more than 10 a.a long and in which no more than two a.a of said continuous sequence are conservatively substituted, said analogues essentially maintaining the binding characteristics of the peptide.

A "substantively higher level of binding" in accordance with the invention will be determined by using any of the binding assays known in the art such as those described below and wherein the measured level of binding of a peptide to a sample obtained from a schizophrenic patient is significantly higher than the measured level of binding of the same peptide to a sample obtained from a non-schizophrenic patient as determined by a suitable statistic test, e.g. Student's T-test.

The term "continuous sequence" concerns an uninterrupted sequence of between 5 and 7 a.a of any of the sequences of SEQ.IDs 1-4 which includes a positively charged a.a at its end. The positively charged a.a is preferably Lysine (indicated as K in the sequences) but may also be Arginine (R) or Histidine (H).

The continuous sequence can be part of a longer peptide of up to 10 a.a., wherein the continuous sequence is situated anywhere in the peptide. In case the peptide consists of more than 7 a.a, wherein the continuous sequence is at one of the peptides ends, said positively charged a.a will be at the open end of the sequence (which is not connected to the additional a.a of the longer peptide) so that the large peptide comprises a positively charged a.a at one of its ends. Wherein the continuous sequence is in the middle of the peptide, the peptide comprises at least one additional positively charged a.a. at one of its ends in addition to the positively charged a.a of the continuous sequence.

Analogues of the above peptides are also within the scope of the present invention. Such analogues are peptides which comprise no more than 10 a.a including at least 5 a.a which have the same sequence as one of the above mentioned continuous sequences but in which one or two a.a are conservatively replaced, as this term is defined below. The analogues also comprise at least one positively charged a.a at their end and essentially maintain the activity of the peptides as this term is defined below.

The term "essentially maintains the binding characteristics" refers to a peptide which level of binding to the tested sample is at least 50%, preferably 70%, most preferably 90% or more than 100% of the level of binding of the peptide to the same tested sample as determined by the same binding assay.

By a preferred embodiment, the invention provides a peptide which binds to a body fluid sample obtained from a schizophrenic patient at a substantively higher level than it binds to a body fluid sample obtained from a non-schizophrenic individual said peptide selected from the group consisting of:

```
i.      LVVGLCK     (SEQ ID NO. 1)
ii.     KLVVGLC     (SEQ ID NO. 2)
iii.    LVVGLMK     (SEQ ID NO. 3)
iv.     KLVVGLM     (SEQ ID NO. 4)
``` or analogs of said peptides in which no more than two a.a are conservatively substituted, said analogues essentially maintaining the binding characteristics of the peptides.

By a most preferred embodiment, a peptide is provided which binds to body fluid samples obtained from a schizophrenic patient substantively higher than it binds to a body fluid sample obtained from a non-schizophrenic individual having the amino acid sequence LVVGLCK (SEQ ID NO. 1).

By an additional aspect of the invention, a peptide is provided which binds to a body sample obtained from a schizophrenic patient substantively higher than it binds to a sample obtained from a non-schizophrenic individual, wherein the peptide binds antibodies that are capable of specific binding to a peptide having the amino acid LVVGLCK. Several non limiting examples of such peptides are the following:

```
i.      KLVVGLC     (SEQ ID NO. 2)
ii.     LVVGLMK     (SEQ ID NO. 3)
iii.    KLVVGLM     (SEQ ID NO. 4)
``` or analogs thereof in which no more than two a.a are conservatively replaced and which maintain the binding characteristics of the peptides.

The letters used above and throughout the present description to denote specific amino acids (a.a.) are in accordance with the one letter a.a. symbols recommended by the IUPAC-IUB Biochemical Nomenclature Commission.

In view of the fact that the peptides of the invention are the putative natural binding sites for autoantibodies found in elevated levels in body fluids of schizophrenic patients, and due to their high purity and high activity, these peptides are most useful for the diagnosis of schizophrenia. Thus, by an additional aspect, the present invention provides an assay for the diagnosis of schizophrenia in an individual comprising the following steps:

(a) obtaining a body fluid sample from said individual being a blood sample, platelet-associated antibodies (PAA) containing fraction thereof, or a fraction containing PAA shed from the platelets;

(b) contacting said sample with a peptide being no more than 10 amino acids (a.a.) long and comprising a continuous sequence of at least 5 amino acids included in any one of the following sequences:

| i.   | LVVGLCK  | (SEQ ID NO. 1) |
| ii.  | KLVVGLC  | (SEQ ID NO. 2) |
| iii. | LVVGLMK  | (SEQ ID NO. 3) |
| iv.  | KLVVGLM; | (SEQ ID NO. 4) | said continuous sequence consisting of at least one positively charged a.a. at one end of said sequence; and said peptide comprising at least one positively charged a.a at its end being the positively charged a.a of said continuous sequence or at least one additional positively charged a.a.; or analogs of said peptide being no more than 10 a.a long and in which no more than two a.a of said continuous sequence are conservatively substituted, said analogues essentially maintaining the binding characteristics of the peptide.

(c) determining the level of binding of said peptide to said sample, a level of binding substantively higher than the level of binding of said peptide to a sample obtained from a non-schizophrenic individual indicating that said tested individual has a high likelihood of having schizophrenia.

By a preferred embodiment, the peptide of step (b) is selected from the group consisting of:

| i.   | LVVGLCK | (SEQ ID NO. 1) |
| ii.  | KLVVGLC | (SEQ ID NO. 2) |
| iii. | LVVGLMK | (SEQ ID NO. 3) |
| iv.  | KLVVGLM | (SEQ ID NO. 4) | or analogs thereof in which no more than two a.a are conservatively replaced and which essentially maintain said peptide's binding characteristics.

By a preferred embodiment, the peptide of step (b) has the amino acid sequence LVVGLCK.

By an additional aspect, the peptides in step (b) are such which bind antibodies which bind peptides having the amino acid sequence LVVGLCK or analogues thereof.

Use of the peptides of the invention and analogues thereof as defined above and below for the preparation of a diagnostic composition for diagnosis of schizophrenia in an individual is also within the scope of the present invention.

By an additional aspect, the invention provides a kit useful in the above assay, said kit comprising a support comprising one or more peptides of the invention immobilized onto it, an anti-human immunoglobulin (hIg) antibody or fragment thereof, or one or more non-based peptides conjugated to a detectable marker which bind to antibodies present in the tested sample, reagents required for carrying out the detection assay wherein said peptides bind to antibodies present in a tested sample as well as instructions for use.

Wherein the detection of the binding of the peptides of the invention to the tested sample is by an anti-hIg antibody the anti-hIg antibody may be conjugated to a detectable marker or alternatively, the kit may also comprise a second type of antibodies directed against said first antibodies, wherein the second antibodies are conjugated to a detectable marker.

By one embodiment, the binding of the peptide of the invention to the tested sample is detected using second non-bound peptides complexed with a detectable marker, said second peptides capable of binding to the antibodies present in the tested sample. In accordance with this embodiment, the detection is achieved by a double antigen sandwich text which may be performed as a one step assay or as a two step assay. Wherein the detection is performed by the double antigen sandwich text assay, the kit of the invention will include such peptides conjugated to a detectable marker instead of the anti-human immunoglobulin antibody.

The assay of the invention may be used as a single test for detecting a high likelihood of schizophrenia in an individual. However, in accordance with an additional aspect of the Invention, the peptides and assay may be used as a confirmatory diagnostic tool. Thus, for example, wherein a high likelihood of schizophrenia is determined in an individual by methods used to date (mainly psychiatric evaluation, as mentioned above), this could be reaffirmed (or, alternatively, re-evaluated) by using the assay of the Invention.

DETAILED DESCRIPTION OF THE INVENTION

Figure 1:
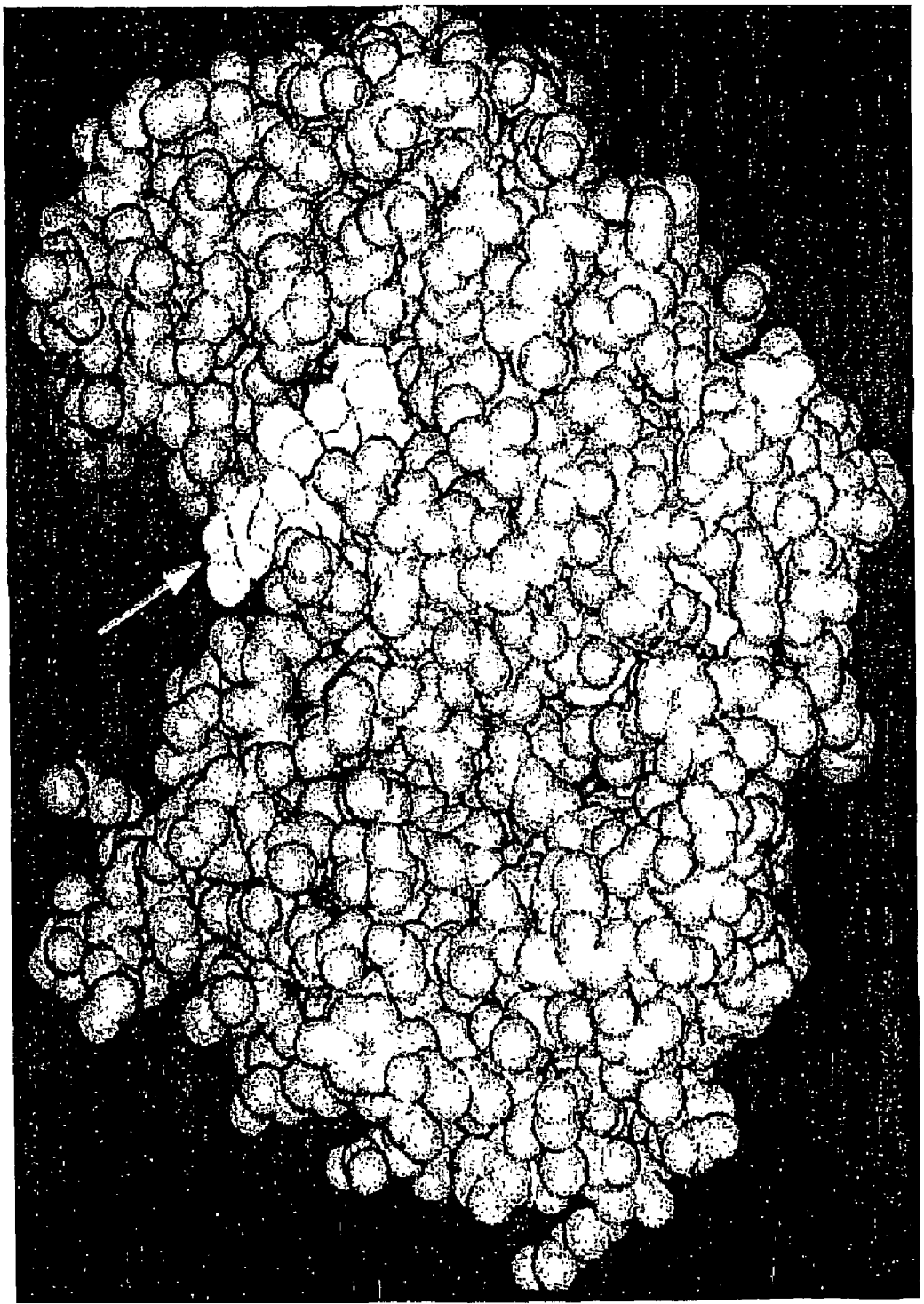
FIG. 1 is a graphical representation showing a surface presentation of enolase which demonstrates that the prior art peptide cannot be the natural binding site for autoantibodies. As can be seen, only arginine R402 (arrow) would be available to binding antibodies wherein the remaining part of the peptide is buried within the protein.
Figure 2:
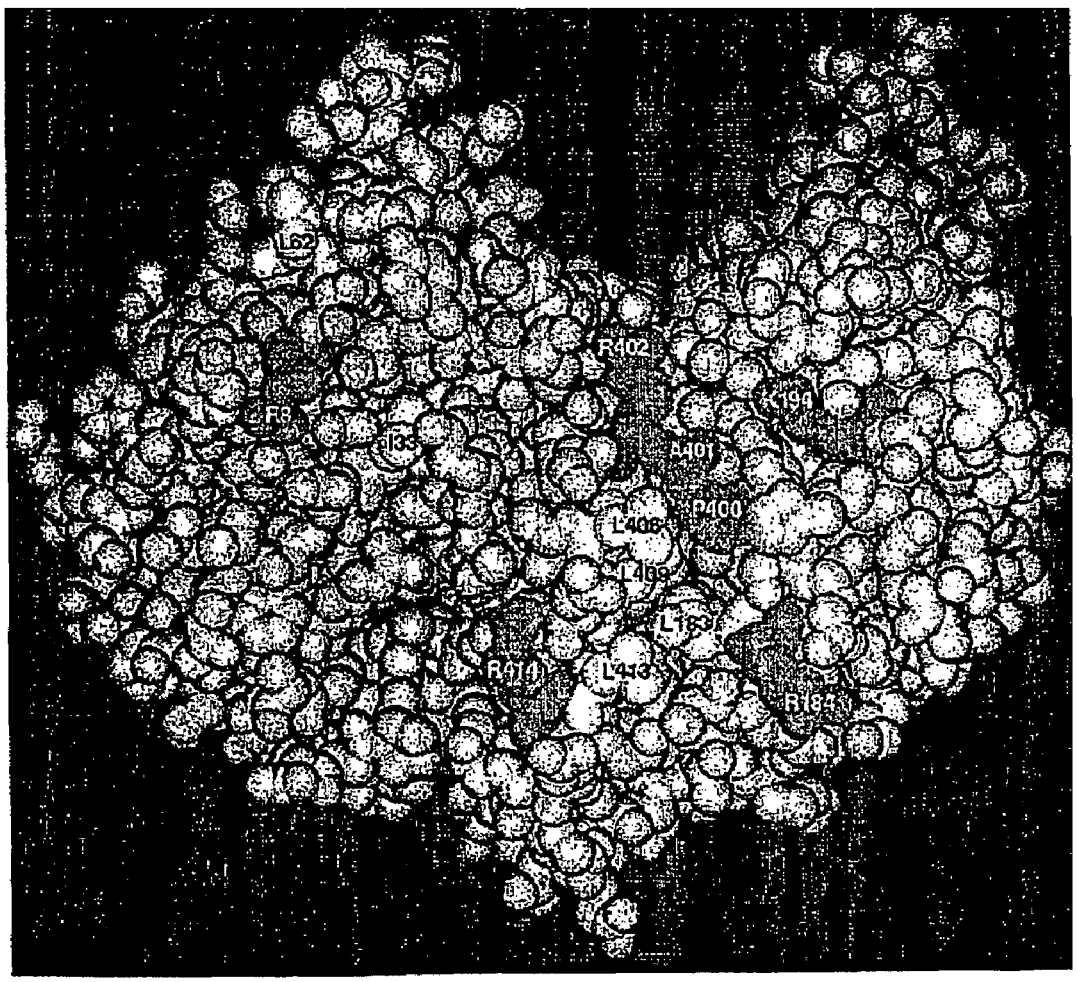
FIG. 2 is a graphical representation of the putative epitope of the peptides of the invention, which consists of six neutral amino acids (L413, L183, L409, L406, P400 and A401) which are surrounded by four positively charged amino acids (R414, R402, R184 and K194).

The present invention provides short highly purified and highly active peptides, which comprise a putative natural epitope of the peptides to which autoantibodies found in elevated levels in schizophrenic patients, bind. The short length of these peptides (7-10 amino acids) and their structure, which is a structure, which can be exposed on the surface of the enolase enzyme in a manner, which enables the autoantibodies to bind to it, render these peptides to be most useful in the diagnosis of schizophrenia. Thus, although the peptides of the prior art (WO 99/51725) were able to bind to autoantibodies present at higher levels in schizophrenic patients as compared to non-schizophrenic individuals, the peptides of the present invention, having the above characteristics enable to detect an individual having a high probability of having schizophrenia more effectively.

The binding activity of the peptide of the invention to various antibodies may be determined by any of the methods known per se such as ELISA or Western Blotting. For example, a tested peptide may be analyzed for its binding activity to antibodies by subjecting it to polyacrylamide gel electrophoresis, blotting it onto PVDS membranes which are then reacted with a body fluid sample of the tested sample and compared to their reaction with a sample obtained from a non-schizophrenic individual.

The extent of binding of the peptides of the invention to PAA can be determined by using any detection system known in the art such as antibodies against human immunoglobulin or fragments thereof linked to a detectable marker. The marker may be a radioactive group, a fluorescent group, an enzyme capable of catalyzing a reaction yielding a detectable product, a biotin group capable of being detected by avidin, etc.

By a preferred embodiment, the extent of binding of the peptides of the invention to the tested sample is carried out using an enzyme immunoassay in which the peptides are labeled with biotin and bound to streptavidine coated tubes as explained below.

In accordance with the invention, it has been found that the position of the positive charge in the peptides may be either at the beginning or at the end of the peptide. This indicates that the peptides exist in an open ring form. In addition it was found that cysteine does not have importance in the sequence of the peptides since substitution of cysteine with Methionin retained the activity of the peptides. Thus, as explained above, the continuous sequence of a.a comprised within the peptide of the invention consists of a positively charged a.a at its end. If the continuous sequence is at one of the ends of the whole peptide, this positively charged a.a will be at one end of the whole peptide. Alternatively, if the continuous sequence is not at the end of the whole peptide, the whole peptide will comprise an additional positive charge at one of its ends.

It is known that the antibody binding site is usually consisted of at least five amino acids. Thus, the peptides of the Invention and their analogues comprise at least five amino acids. The five amino acids will be such which appear consecutively in one of the continuous sequences of the invention.

In order to maintain the binding characteristics of the peptide, the analogues of the invention comprise no more than two a.a. substitutions which are conservative substitutions. These are substitutions in which an amino acid of one class is replaced by an amino acid of the same class, where a class is defined by common physiochemical amino acid chain properties such as charge, size or hydrophobicity. Amino acids of the same class are characterized by high substitution frequencies in homologous proteins found in nature (as determined, for example, by a standard Dayhoff frequency exchange matrix).

Thus for example the leucine positioned in the first position of the amino acid sequence of a peptide of the invention may be conservatively substituted by the amino acids glycine or valine, which belong to the same family of amino acids, without altering the binding activity of the peptide. The positively charged a.a at the end of the peptide of the invention may be conservatively replaced by another positively charged a.a. A person versed in the art will have no difficulty in determining by which amino acid each of the amino acids of the peptide may be replaced in accordance with the known grouping of amino acids into families as may be found, for example, in Molecular Biology of the Cell Editors Alberts B. et al., Garland Publishing, Inc., New York and London, 2nd Edition, 1989, pages 54-55.

The peptides of the invention may also be chemically modified. In such a chemically modified peptide at least one of the amino acid residues may be modified either by a natural process such as post-translational modification or by chemical modification techniques which are well known in the art. Examples of chemical modifications are acetylations and glycolysations, glycosamine-glycinations, ADP-ribosylations, covalent attachment of a lipid or a lipid derivative, methylation, myristylation, pegylation, phosphorylation, etc. The chemical modification may be at the peptide's amino end or at the carboxy end.

The peptides of the invention may additionally have a non peptide component attached such as for example a macromolecular carrier group which may covalently be attached to the amino or carboxy side of the peptide. Such a carrier may for example be polyethylene glycol, carbohydrates or lipid fatty acid conjugates.

All the above describe changes in the peptides of the invention that may result in increased stability, bioavailability or activity of the peptides of the invention.

The peptide of the invention may be obtained by enzymatic digestion (e.g. using Clostrapain) or chemical (CNBr) digestion of a longer protein. In such a case, the resulting peptides are separated by methods known in the art such as by RP-HPLC and the separate peptides may then be used for sequencing (e.g. by Eurosequence b.v. (Nijenborgh 4; 9749 Gronigen; The Netherlands)) and analyzed for their binding capability to antibodies as described above.

The short length of the peptides of the Invention (5 to 10 a.a) renders them as very good candidates for synthesize by methods known in the art such as on Abimed 522 at a 10 µmol scale by Eurosequence b.v. (see detailed explanation in the examples below). The binding activity of the newly synthesized peptides will be determined using any of the assays mentioned above.

Another advantages of the present invention, which is based on the fact that the peptides of the invention are short, purified and active peptides, is that the "body fluid" sample of the individual to be tested may be a blood plasma or serum sample which is relatively easy to obtain and prepare. However, at times it may be advantageous to perform the assay of the invention on a blood sample obtained from the tested individual which is a PAA containing fraction obtained from the sample by any of the methods known in the art, such as by obtaining a platelet-rich plasma and isolating PAA therefrom. In accordance with the invention, the sample may also be any other body fluid sample obtained from the tested individual including a whole blood sample, or any other body fluid sample containing PAA, e.g. saliva, cerebrospinal fluid, etc. Chemical analysis as well as immunoactivity assays in accordance with the invention showed that the peptide having the amino acid sequence LVVGLCK had the highest purity of synthesis and could spontaneously form dimers thus doubling the epitope per binding site of streptavidine and enhancing the binding potential of PAAs to this peptide. Therefore, in accordance with the invention, a peptide having the above sequence or a peptide comprising this sequence are preferred for use in the diagnosis of schizophrenia in accordance with the invention.

EXAMPLES

The invention will now be demonstrated by the following non limiting Examples with reference to the figures.

Materials and Methods

1. Patients and control persons—Thirty-nine schizophrenic patients participated in this study. The following parameters were recorded: gender, age, duration of schizophrenia, number of hospitalizations, years of education and the psychiatric status (PANSS). Fifty plasma samples were obtained from a local blood bank.

2. Plasma—Venous blood was drawn with heparin as coagulant from patients and control subjects. Plasma was obtained after centrifugation (4000 g; 15 mins. 4° C.).
3. Peptide synthesis and biotin labeling—The peptides were synthesized on an Abimed 522 at a 10 micromol scale by Eurosequence b.v., (Nijenborgh 4: 9747 AG Groningen; The Netherlands) and labeled at the amino terminal with biotin containing a six carbon spacer. Peptide purity was routinely assessed by RP-HPLC and, when considered necessary, by laser desorption mass spectroscopy. The peptides were routinely dissolved in 1 ml water/DMF/DMSO (1:1:1; v/v/v).
4. Line blot—peptides were line blotted onto PVDF or nitrocellulose membranes. Membrane strips were incubated overnight with 0.5 ml plasma sample in 0.5 ml buffer (200 mM Tris; 0.3% Casein; 200 mM KCl; 10.6 mM phenol; 2.1 mM $CaCl_2$; 0.01% Triton X-100; pH 8.5) at room temperature under gentle shaking in BioRad incubation arrays. After three washings with PBS, strips were probed with Anti-human Fc (goat) conjugated to horseradish peroxidase (SIGMA; dilution 1:100) for 2 hours at room temperature under gentle shaking. Fast-DAB™ or 4-Chloro-naphthol (SIGMA) were used as color reagent to detect bound antibodies.
5. Enzyme immuno assay—Streptavidine coated tubes (Boehringer Mannheim; 80 nMol Streptavidine per tube) were coated with a tenfold excess of biotin-labeled peptide in 1 ml PBS for 3 days at 4° C., washed twice with 2 ml 1M NaCl, once with 2 ml water, dried and stored under vacuum at minus 18° C. until use. For the test, 0.05 ml sample and 1 ml Incubation Buffer (60 mM citric acid; 90 mM $Na_2HPO_4$; 168 mM NaOH; 200 mM NaCl; pH 7.7) are added to the peptide labeled tube and incubated for 1 hr at 37° C. without shaking. The tubes were covered in order to prevent evaporation. The tubes were then washed three times with 2 ml 1 M NaCl solution for 15 min. under gentle shaking, 1 ml Anti-human Fc (goat) conjugated to horseradish peroxidase (SIGMA) added at a dilution of 1:2000 in POD Buffer (200 mM Tris; 0.3% Casein; 200 mM KCl; 10.6 mM phenol; 2.1 mM $CaCl_2$; 0.01% Triton X-100; pH 8.0) and incubated for 0.5 hr at 37° C. without shaking. After 4 washings with 2 ml 1M NaCl solution, the color reaction was initiated by adding 1 ml Tetramethylbenzidine (TMB) Liquid Substrate System™ (SIGMA). The enzymatic reaction was stopped by adding 1 ml 0.5M $H_2SO_4$. The absorbence was read at 450 nm spectrophotometrically.

Example 1

Four peptides in accordance with the invention, having one of the a.a. sequences:

(a) LVVGLCK
(b) KLVVGLC
(c) LVVGLMK
(d) KLVVGLM were biotin-labeled and coated onto streptavidine coated tubes as described above. A pool of plasma samples was prepared from 5 schizophrenic patients and an additional pool of plasma was prepared from 5 non-schizophrenic individuals.

Results:
All of the four peptides of the invention bound to the plasma pool originating from schizophrenic patients to a higher extent than their binding to the control plasma sample obtained from non-schizophrenic individuals (as measured in the enzyme immunoassay described above which showed 0.5 O.D. in the samples of the peptides with the control plasma samples and 1.6 O.D. in the samples of the peptides with the schizophrenia derived plasma pool).

Example 2

Diagnosis of Schizophrenia Using the Peptide LVVGLCK

Of the four peptides of the invention, the highest purity of synthesis was found in the peptide LVVGLCK. In addition, these peptides were found to spontaneously form dimers, thus doubling the epitope for binding site of streptavidine.

Therefore, an experiment was carried out with the biotin-LVVGLCK as follows: the peptide was biotin-labeled and coated onto streptavidine coated tubes as explained above. Plasma samples of 39 schizophrenic patients and 50 control non schizophrenic individuals were tested with the coated peptide and the level of binding was determined by the enzyme immunoassay described above.

Figure 3:
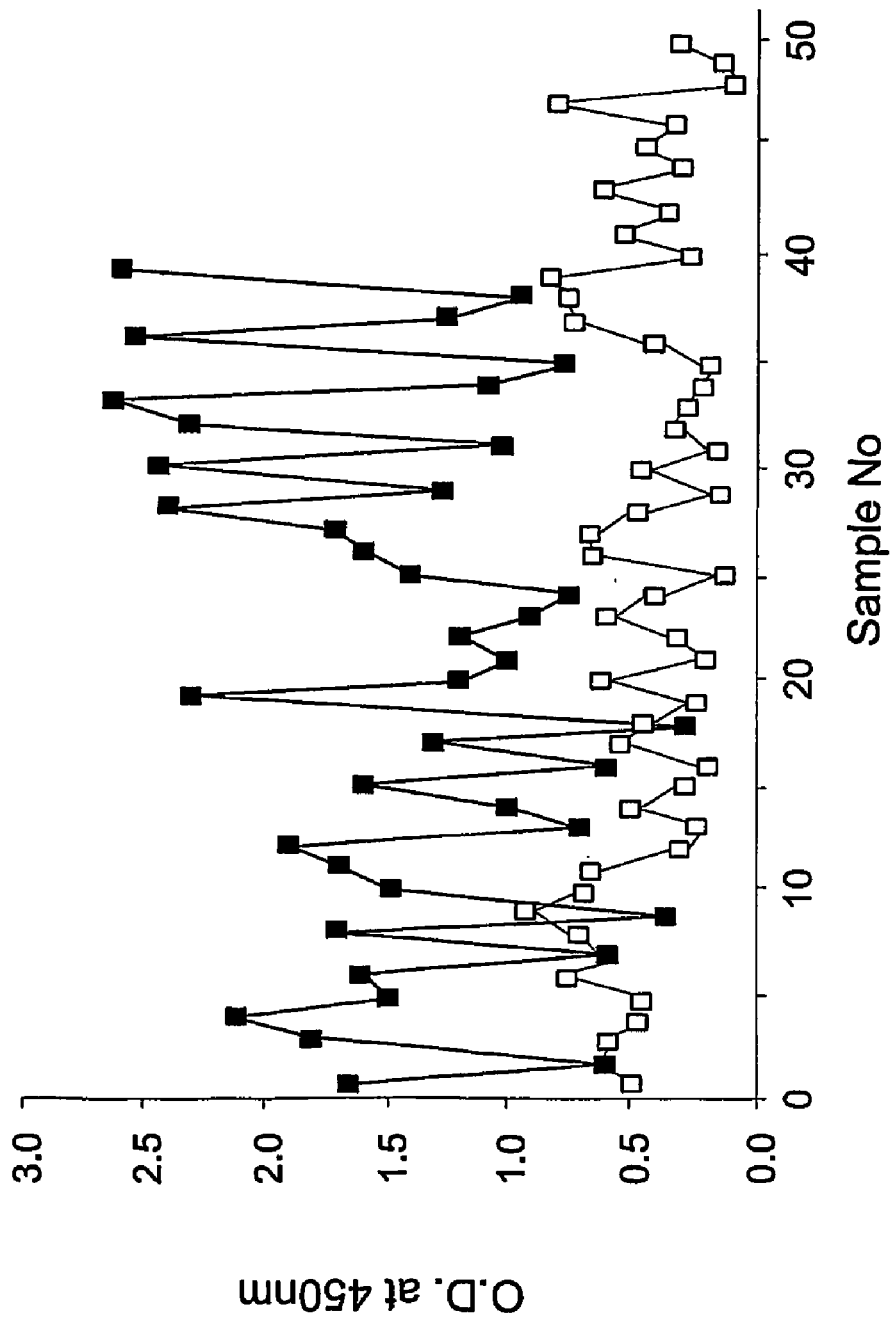
FIG. 3 is a schematic representation showing the level of binding of plasma samples from 39 schizophrenic patients (filled squares) and 50 non schizophrenic individuals (open squares) with the biotinylated peptide LVVGLCK in an enzyme immunoassay.

As seen in FIG. 3, the biotinylated peptide LVVGLCK bound to a higher extent to the plasma samples obtained from schizophrenic patients (filled squares) at a mean value and standard deviation of 1.47±0.65 as compared to its binding to plasma samples from non schizophrenic individuals (open squares) with mean value and standard deviation amounting to 0.46±0.21. The difference of binding of this peptide to the two groups was statistically highly significant ($1.1 \times 10^{-11}$ using Student's T-test).

Example 3

Figure 4:
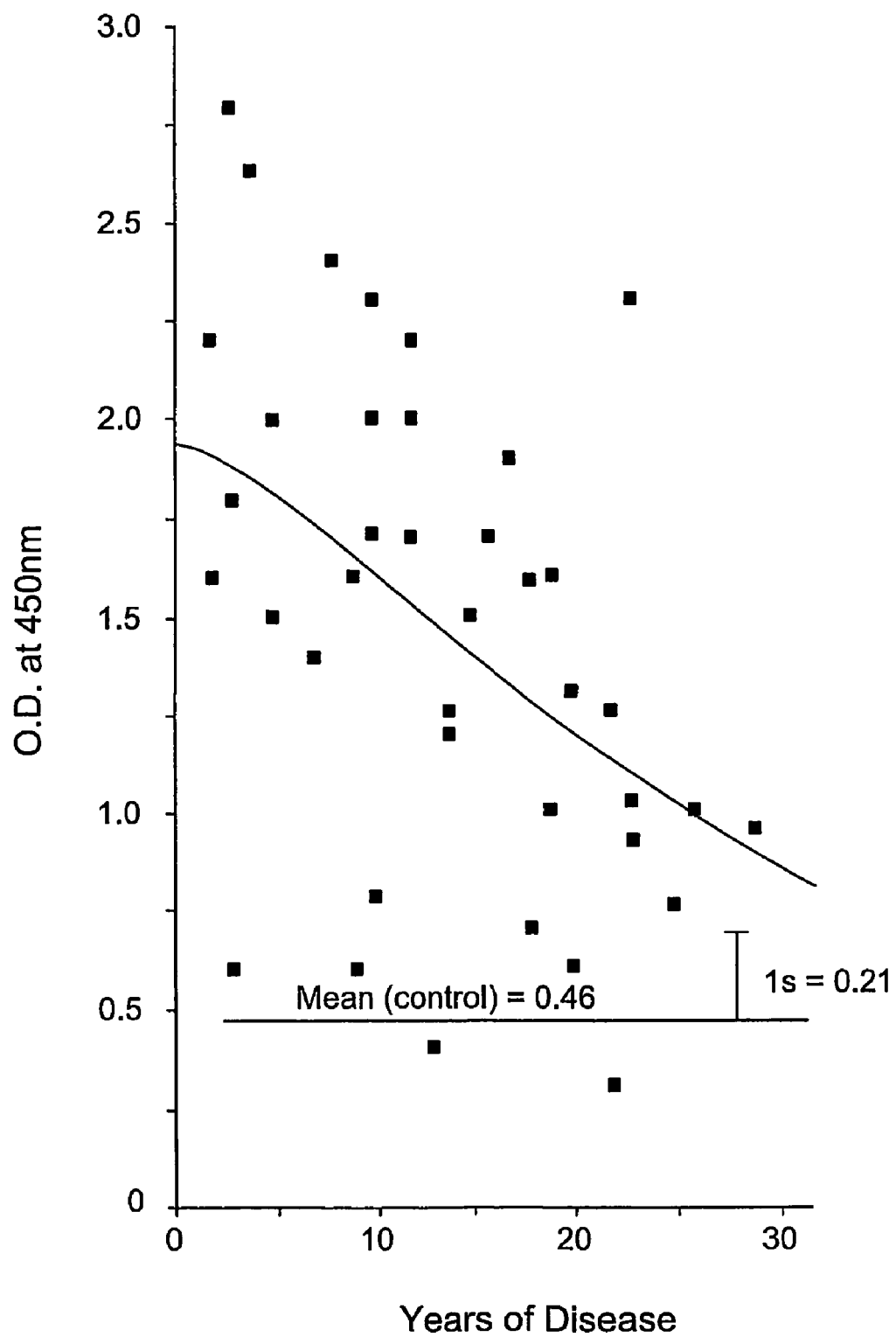
FIG. 4 is a schematic representation showing an inverse correlation between the O.D. values measured in the enzyme immunoassay described above in samples obtained from schizophrenic patients and the duration of the disease in these patients.

Analysis of Schizophrenia on the Basis of the Peptide of the Invention as Compared to Acceptable Psychiatric Analysis By further analysis of the results described in Example 2 above, with other recorded psychiatric parameters of the patients, an inverse correlation was found between the duration of schizophrenia and the level of binding to the peptide of the invention measured as optical density (O.D.). A geometric fit ($y=ax^{bx}$) was applied with $a=1.9376$ and $b=0.000798$ as coefficients (FIG. 4). Summarizing FIGS. 3 and 4, the following results shown in Table 1 below can be reached by comparing the biochemical test with the psychiatric evaluation.

TABLE 1

|  | | Biochemical Test | | | |
| --- | --- | --- | --- | --- | --- |
| Psychiatric Evaluation | | 1-15 years disease | 16-30 years disease | 1-30 years disease | Controls |
| No. of tested individuals | N = 39 | N = 23 | N = 16 | N = 39 | N = 50 |
| Schizophrenic: | 39 | 19 | 7 | 26 | 0 |
| Borderline: | 0 | 1 | 6 | 7 | 6 |
| Negative | 0 | 3 | 3 | 6 | 44 |

This takes the following definitions into account:
Negative: 0 until mean +1s
Borderline: Between mean +1s until mean +2s
Positive: Higher than mean +2s In conclusion, a sensitivity of better than 80% and a specificity of better than 90% seem to be feasible. However, it should be noted that these definitions are arbitrary and may, therefore, be changed depending whether the emphasis is more on specificity or on sensitivity.

said sequence consisting of at least one positively charged a.a. at one end of said sequence; and wherein said peptide optionally comprises at least one additional positively charged a.a. at its end.

The invention claimed is:

1. An isolated peptide which binds to a body fluid sample obtained from a schizophrenic patient at a higher level than its binding to a body fluid sample obtained from a non-schizophrenic individual, said peptide being no more than 10 amino acids (a.a.) long and comprising one of the sequences selected from the group consisting of:

|      |           |                |
|------|-----------|----------------|
| i.   | LVVGLCK,  | (SEQ ID NO. 1) |
| ii.  | KLVVGLC,  | (SEQ ID NO. 2) |
| iii. | LVVGLMK, and | (SEQ ID NO. 3) |
| iv.  | KLVVGLM;  | (SEQ ID NO. 4) |

2. An isolated peptide which binds to a body fluid sample obtained from a schizophrenic patient at a higher level than it binds to a body fluid sample obtained from a non-schizophrenic individual said peptide selected from the group consisting of:

|      |           |                |
|------|-----------|----------------|
| i.   | LVVGLCK,  | (SEQ ID NO. 1) |
| ii.  | KLVVGLC,  | (SEQ ID NO. 2) |
| iii. | LVVGLMK, and | (SEQ ID NO. 3) |
| iv.  | KLVVGLM.  | (SEQ ID NO. 4) |

3. An isolated peptide which binds to body fluid samples obtained from a schizophrenic patient at a higher level than it binds to a body fluid sample obtained from a non-schizophrenic individual, said peptide consisting of the amino acid sequence LVVGLCK (SEQ ID NO.1).

4. An assay for the diagnosis of schizophrenia in an individual comprising the following steps:
(a) obtaining a body fluid sample from said individual being a blood sample, a platelet-associated antibodies (PAA)-containing fraction thereof, or a fraction containing PAAs shed from the platelets;
(b) contacting said sample with a peptide being no more than 10 amino acids (a.a) long and comprising one of the sequences selected from the group consisting of:

| i. | LVVGLCK, | (SEQ ID NO. 1) |
| ii. | KLVVGLC, | (SEQ ID NO. 2) |
| iii. | LVVGLMK, and | (SEQ ID NO. 3) |
| iv. | KLVVGLM; | (SEQ ID NO. 4) | said sequence consisting of at least one positively charged a.a. at one end of said sequence; and wherein said peptide comprises at least one additional positively charged a.a. at its end;
(c) determining the level of binding of said peptide to said sample, wherein a higher level of binding than the binding level of said peptide to a sample obtained from a non-schizophrenic individual indicating that said tested individual has a high likelihood of having schizophrenia.

5. The assay according to claim 4, wherein the peptide of step (b) is selected from the group consisting of:

| i. | LVVGLCK, | (SEQ ID NO. 1) |
| ii. | KLVVGLC, | (SEQ ID NO. 2) |
| iii. | LVVGLMK, and | (SEQ ID NO. 3) |
| iv. | KLVVGLM. | (SEQ ID NO. 4) |

6. The assay according to claim 4, wherein the peptide of step (b) consists of the amino acid sequence LVVGLCK (SEQ ID NO.1).

7. The assay according to claim 4, wherein the peptide in step (b) binds antibodies which bind peptides consisting of the amino acid sequence LVVGLCK (SEQ ID NO.1).

8. The assay of claim 4, for use in confirming schizophrenia in the individual.

9. A kit for use in the diagnosis of schizophrenia comprising:
a support comprising one or more peptides of claim 1 immobilized thereon;
anti-human immunoglobulin (anti-hIg) antibody or fragment thereof; and
instructions for use.

10. The kit according to claim 9, wherein said anti-hIg antibody is complexed to a detectable marker.

11. A kit for use in the diagnosis of schizophrenia comprising:
a support comprising one or more peptide of claim 1 immobilized thereon;
one or more peptides of claim 1, which are non-bound to the support, and which are complexed to a detectable marker;
and instructions for use.

* * * * *